(12) United States Patent
Tan

(10) Patent No.: US 7,646,485 B2
(45) Date of Patent: Jan. 12, 2010

(54) METHOD AND APPARATUS FOR ENHANCING THE ACCURACY OF CRDS MEASUREMENTS

(75) Inventor: Sze Tan, Sunnyvale, CA (US)

(73) Assignee: Picarro, Inc., Sunnyvale, CA (US)

( * ) Notice: Subject to any disclaimer, the term of this patent is extended or adjusted under 35 U.S.C. 154(b) by 1202 days.

(21) Appl. No.: 11/002,603

(22) Filed: Dec. 2, 2004

(65) Prior Publication Data

US 2009/0066956 A1   Mar. 12, 2009

(51) Int. Cl.
G01N 21/61 (2006.01)
(52) U.S. Cl. .................................... 356/437
(58) Field of Classification Search ......... 356/432–440; 372/9, 33
See application file for complete search history.

(56) References Cited

U.S. PATENT DOCUMENTS

| 6,233,052 B1* | 5/2001 | Zare et al. ................... 356/437 |
| 7,323,677 B1* | 1/2008 | Wang ..................... 250/227.14 |
| 2003/0189711 A1* | 10/2003 | Orr et al. ..................... 356/484 |
| 2004/0061859 A1* | 4/2004 | Taubman ..................... 356/437 |
| 2005/0206903 A1* | 9/2005 | Tan et al. ..................... 356/437 |
| 2005/0254056 A1* | 11/2005 | Kachanov et al. ........... 356/437 |
| 2006/0181710 A1* | 8/2006 | Kachanov et al. ........... 356/437 |

* cited by examiner

Primary Examiner—Hoa Q Pham
(74) Attorney, Agent, or Firm—Lumen Patent Firm

(57) ABSTRACT

A method and apparatus for enhancing the accuracy of spectroscopic measurements using a cavity ringdown spectrometer (CRDS) is provided. A first aspect of the invention consists of a novel algorithm for the processing of ring-down data that significantly reduces the amplitude of an exponential fitting artifact, and thereby gives a better estimate of the actual loss. The primary cause of the artifact is the presence of an unwanted backwards-traveling wave that counter-propagates within the ringdown cavity. Scattering due to small imperfections at the cavity mirrors produces this wave and its intensity may be minimized by adjustment of the mirror positions during cavity construction. A second aspect of the invention consists of an apparatus for measuring the backscattered wave within a cavity to allow such cavity mirror adjustments to be made.

5 Claims, 4 Drawing Sheets

METHOD AND APPARATUS FOR ENHANCING THE ACCURACY OF CRDS MEASUREMENTS

FIELD OF THE INVENTION

This invention relates to a method and apparatus for enhancing the accuracy of spectroscopic measurements using a cavity ringdown spectrometer (CRDS).

BACKGROUND OF THE INVENTION

CRDS is known to be a highly accurate spectroscopic technique. In the most advantageous implementation of CRDS, a three or four mirror ring cavity is used. The cavity mirrors must have very high reflectivity and low loss in order to achieve a high cavity finesse.

Light is coupled into the cavity to excite a forward-propagating wave that decays when the light source is interrupted. If one assumes that light only travels in one direction around the cavity, the intensity of the light exiting the cavity after the light source is interrupted decays exponentially with time. The time constant ($\tau$) of the exponential decay gives an absolute measurement of the total loss suffered by the light as it traverses the cavity. By measuring the variation in the time constant for a number of ringdown events obtained as the input light is tuned over a range of wavelengths, a spectrum of the absorption of the analyte species present in the optical cavity is obtained. From such an absorption spectrum, the concentrations of the analyte(s) contained within the gas inside the cavity may be determined via a spectral-fitting procedure.

BRIEF DESCRIPTION OF THE INVENTION

FIG. 1 is a typical example of a spectrum measured from a cavity that is continually maintained at low pressure using, for example, a vacuum pump. The wavelength of the input light is varied by temperature tuning a diode laser. Standard exponential fitting was used to extract the time constants from the ringdown waveforms. Under ideal conditions, there would be no absorption due to the vacuum within the cavity. However, in FIG. 1 several sharp, low-amplitude absorption lines can still be seen, which lines are due to trace quantities of substances that were not completely removed by the evacuation pumping. More importantly, the baseline of the spectrum oscillates as the wavelength of the radiation changes. Such a variation in the baseline can hide small peaks and make spectral fitting problematic. I have determined that there is no physical mechanism for producing such a variation in absorption, and that it is an artifact caused by the inappropriate use of exponential fitting for determining the loss.

A first aspect of the invention consists of a novel algorithm for the processing of ring-down data that significantly reduces the amplitude of the artifact, and thereby gives a better estimate of the actual loss. Although the algorithm succeeds in reducing the artifact, it does so at the cost of increasing somewhat the uncertainty in the measured loss. It is therefore preferable to construct cavities for which the artifact is as small as possible. I have identified the primary cause of the artifact to be the presence of an unwanted backwards-traveling wave that counter-propagates within the ringdown cavity. Scattering due to small imperfections at the cavity mirrors produces this wave and its intensity may be minimized by adjustment of the mirror positions during cavity construction. A second aspect of the invention consists of an apparatus for measuring the backscattered wave within a cavity to allow such cavity mirror adjustments to be made.

DETAILED DESCRIPTION OF THE INVENTION

When a cavity is filled so that exactly one mode is excited, the intensity of the light in the cavity decays exponentially after the excitation is ended. When a ring cavity (e.g., three or four mirror) is used, a mode corresponds to a wave with a specific polarization and spatial profile that propagates in one direction around the cavity. In a cavity ring-down spectrometer, the light entering the cavity is aligned and shaped so as to excite only a single cavity mode. The common practice of fitting the ring-down waveform by an exponential in order to determine the time constant and the loss within the cavity is based on the assumption that only a single mode has been excited.

By carefully examining the ring-down waveform collected at the output of the cavity when the input light to the cavity is turned off, I have determined that this assumption is often invalid. The input light couples most strongly to a mode that propagates in one direction around the cavity (the "forward-propagating" mode), but as this light propagates, it scatters off even tiny imperfections on the cavity mirrors and generates light which couples into a backwards-propagating mode. This backwards propagating mode also propagates resonantly within the cavity. While the cavity is being filled, the amplitude of the backwards wave is very small in comparison to the forward driven wave, but during the ring-down period, I have found that a non-negligible amplitude of backwards-propagating light can be generated. Due to the weak coupling between the forwards and backwards waves during the ring-down period, the ring-down waveform is no longer precisely exponential. In order to determine the loss from the non-exponential waveform, I have developed a modified fitting procedure.

Figure 2:
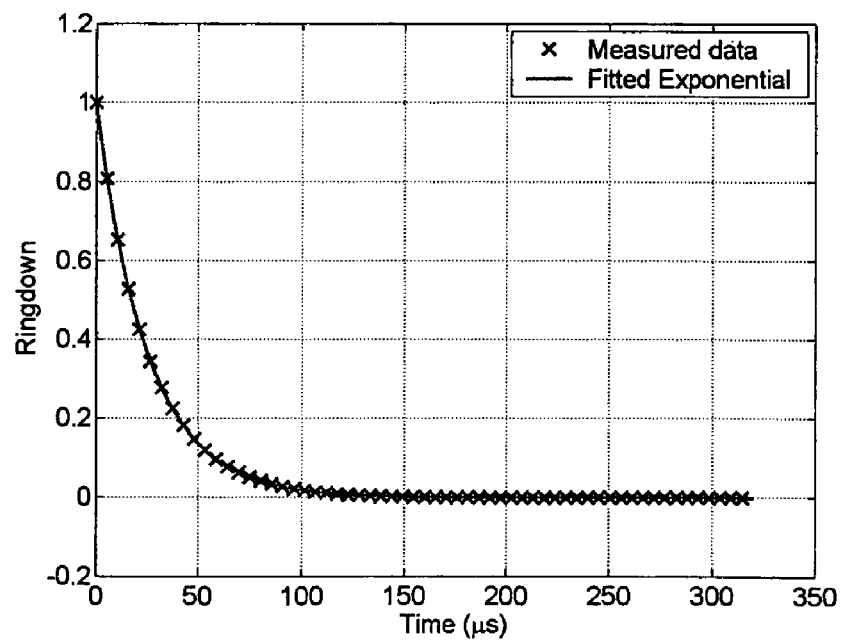
FIG. 2 shows a ring-down waveform and least squares fitted exponential decay waveform. For clarity, only every fiftieth point of the measured ring-down waveform is shown.
Figure 3:
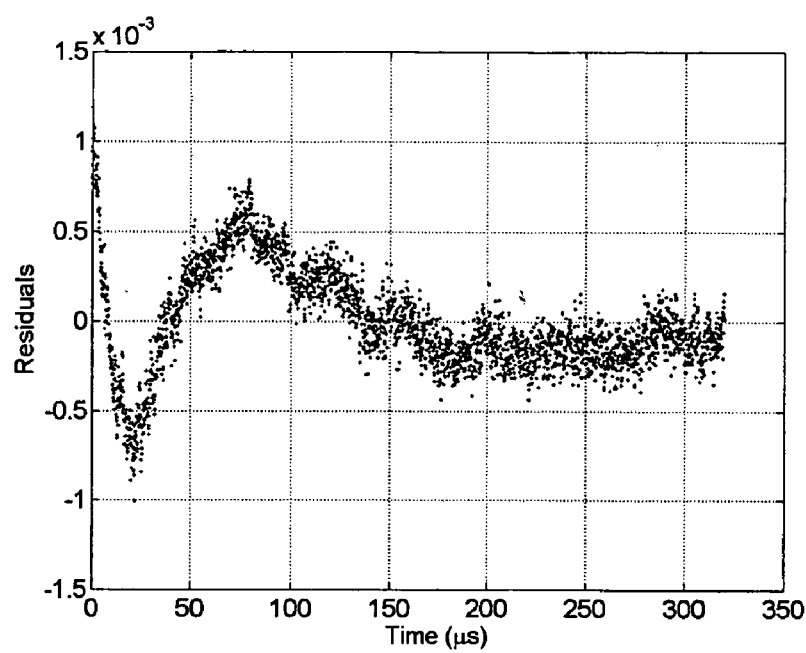
FIG. 3 shows the residuals from the exponential fitting vs. the measured data.

FIG. 2 shows the ring-down waveform collected from a typical CRDS instrument using a ring cavity. On this scale, it appears to be an exponential decay and indeed appears to be indistinguishable from the least squares fitted exponential curve that is also shown on the same axes. In order to show that the actual ring-down curve is not precisely exponential, the residuals of the fit are plotted in FIG. 3. These are defined as the difference between the measured data and the least squares exponential fit. From FIG. 3 it is evident that there is a systematic component, not accounted for by the exponential fit, that is significantly larger than the measurement noise.

In order to understand the nature of the residuals, I considered a mathematical model for the scattering of light into the backwards-propagating mode, and calculated how the intensity of the forwards-propagating mode (and hence the ring-down waveform) is affected by this mechanism. We may approximate the cavity field by the sum of a forward propagating field of amplitude $E_F$ and a backward propagating field of amplitude $E_B$ that are weakly coupled by the scattering. During the ring-down period, when there is no incoming light, it is expected that the differential equations satisfied by these amplitudes have the form:

$$\frac{dE_F}{dt} = -\gamma E_F + \kappa E_B \qquad (1)$$
$$\frac{dE_B}{dt} = -\gamma E_B + \kappa E_F$$

where the constant $\gamma$ represents the field decay rate due to mirror and other losses and $\kappa$ represents the coupling between the fields. Since the coupling may be due to scattering contributions from all the cavity mirrors, the coupling coefficient $\kappa$ will in general be wavelength dependent, as the scattered waves can interfere. The coefficients in the two equations are taken to be equal, which is plausible in view of the symmetry of the forward and backwards propagation during the ring-down period. In general, both $\gamma$ and $\kappa$ are complex numbers.

Solving these differential equations subject to the initial conditions $E_F(0)=1$ and $E_B(0)=0$ gives:

$$E_F = \frac{1}{2}[e^{-(\gamma-\kappa)t} + e^{-(\gamma+\kappa)t}] \text{ and } E_B = \frac{1}{2}[e^{-(\gamma-\kappa)t} - e^{-(\gamma+\kappa)t}]. \qquad (2)$$

The monitored ringdown waveform $I_F$ is the intensity of the forward wave (scaled by the transmission of the output mirror). This may be written in terms of the field as $$I_F=|E_F|^2=\exp(-2\gamma_r t)|\cos h\,\kappa t|^2=\exp(-2\gamma_r t)[\sin h^2\kappa_r t+\cos^2\kappa_i t], \qquad (3)$$

where we have written $\kappa=\kappa_r+i\kappa_i$, and $\gamma_r$ is the real part of the complex number $\gamma$.

When the coupling between the forwards and backwards-propagating modes is small, $|\kappa|<<|\gamma|$, and $I_F$ closely resembles an exponential decay with time constant $(2\gamma_r)^{-1}$. This explains the usefulness of exponential fitting for the approximate analysis of ring-down data. From the results shown in FIG. 3, however, it is evident that the deviation from the true exponential can be significant.

The nature of the deviation from the exponential form may be found by expanding the term in square brackets in Equation (3) as a Taylor series for small t, (time)

$$\sin h^2\kappa_r t+\cos^2\kappa_i t\approx 1+(\kappa_r^2-\kappa_i^2)t^2+O(t^4) \qquad (4)$$

We may then approximate $$I_F\approx\exp(-2\gamma_r t)+(\kappa_r^2-\kappa_i^2)t^2\exp(-2\gamma_r t)+ \qquad (5)$$

This demonstrates that a better fit to the ring-down waveform may be obtained by using an expression for $I_F$ which contains terms involving $\exp(-2\gamma_r t)$ and $t^2 \exp(-2\gamma_r t)$, the amplitudes B and D of these terms being chosen to fit the data. We thus consider $$I_F(t) = A + B\,\exp\left(-\frac{t}{\tau}\right) + Dt^2\exp\left(-\frac{t}{\tau}\right) \qquad (6)$$

where $\tau=(2\gamma_r)^{-1}$, and the constant A is used to account for any offset in the electronics. The value of $\tau$ calculated by this algorithm is a better estimate of the decay time constant due to absorption than that found by incorrectly assuming the ring-down to be a pure exponential.

Figure 1:
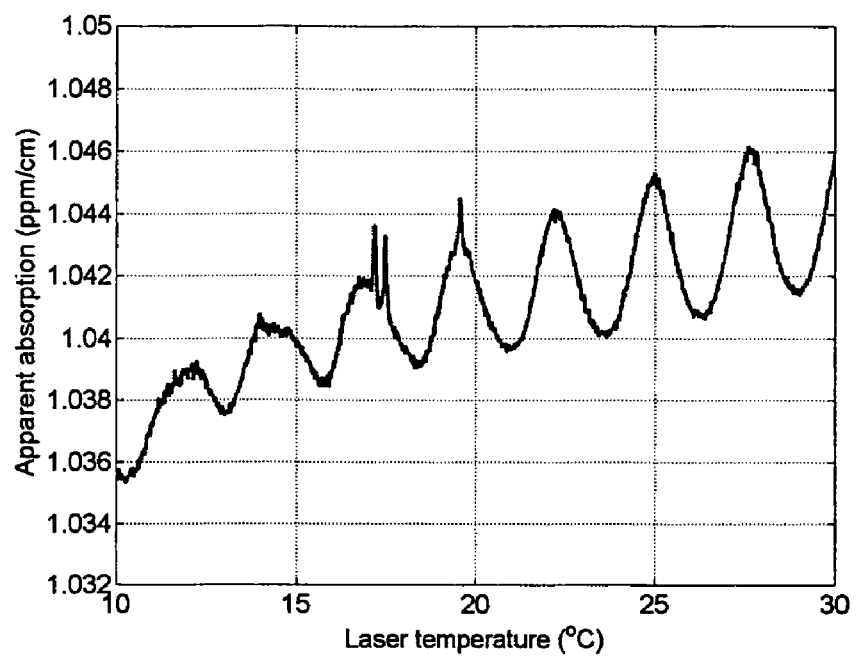
FIG. 1 shows the apparent absorption spectrum of a ring-down cavity using exponential fitting when the temperature of the laser is varied.
Figure 4:
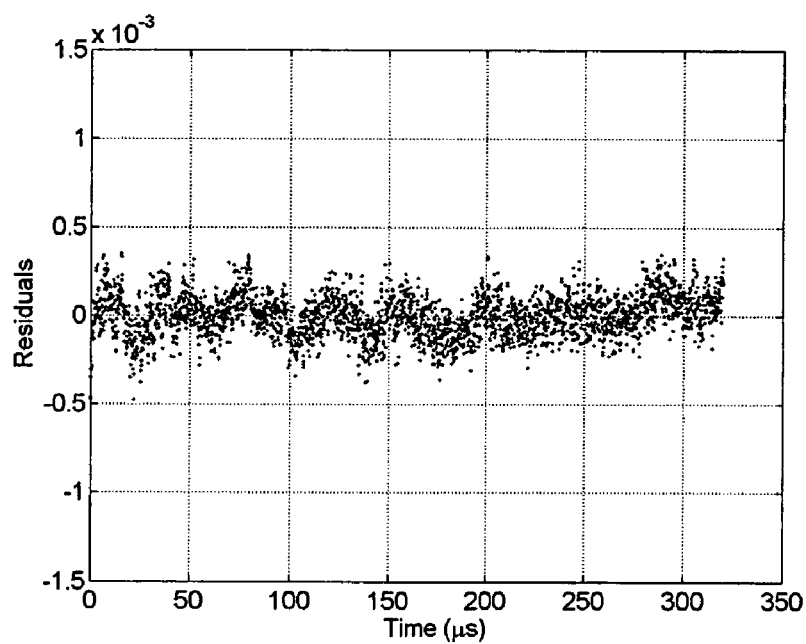
FIG. 4 shows the residuals using the novel fitting algorithm in accordance with the present invention.
Figure 5:
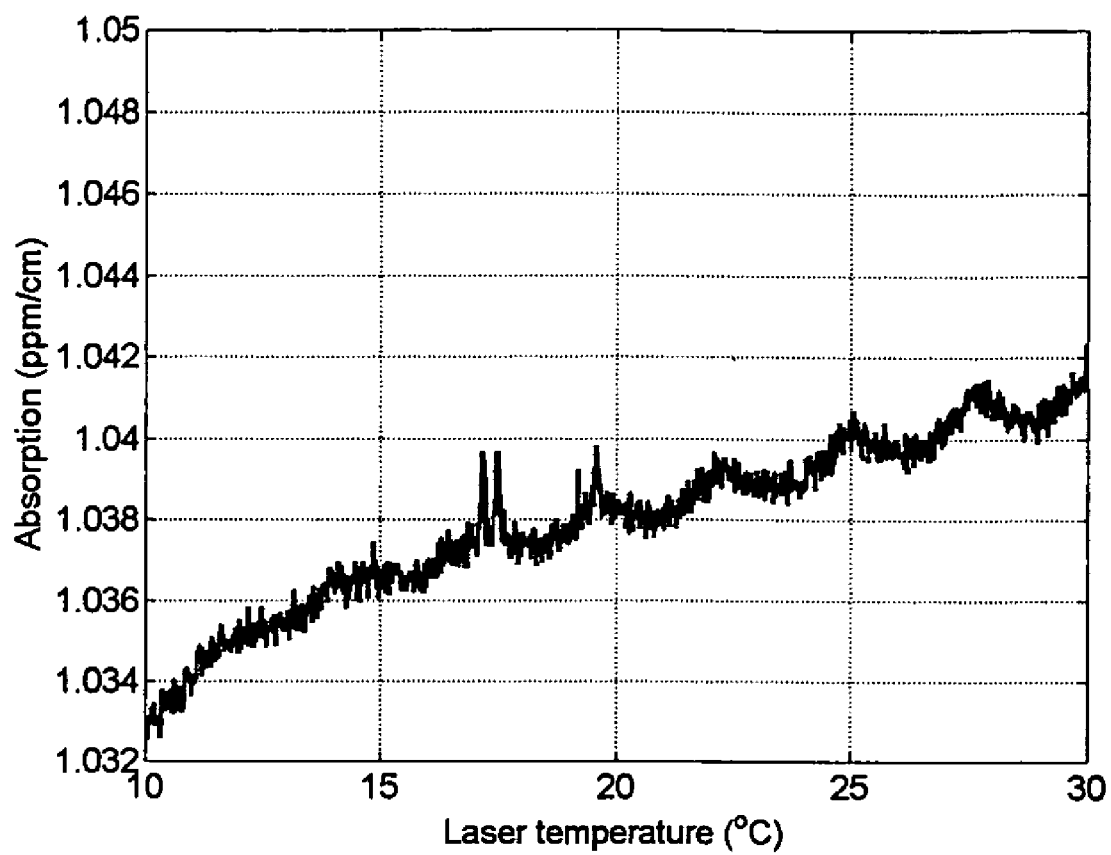
FIG. 5 shows the absorption spectrum for the same ring-down cavity used for FIG. 1, but with the data processed using a fitting algorithm in accordance with the present invention.

When the ring-down data shown in FIG. 2 are fitted in a least squares sense using these functions and the residuals of the fit are calculated, the result is shown in FIG. 4. Comparing these with those found for pure exponential fitting (shown in FIG. 3), it is evident that the large systematic variation has been removed, and also that the residuals for the new fitting algorithm are now dominated by the measurement uncertainties. In order to demonstrate that the value of the calculated decay time constant is now a better indication of the true cavity loss, the absorption spectrum for the data of FIG. 1 was recalculated by repeated application of the algorithm. The result of this calculation is shown in FIG. 5. The oscillations in the baseline, which were originally larger than the absorption peaks, have now been substantially reduced, making it easier to observe the precise spectrum of the gas in the cavity.

I now give a detailed description of the algorithm, which is computationally efficient, so that it can be used for real-time processing of ring-down data to afford an accurate measure of $\tau$. Given that the ring-down waveform $I_F$ in equation (6) is sampled at intervals separated by T to give the sequence of points $I_F[kT]$, for k=0, 1, 2, . . . , N−1 we wish to find quantities $\tau$, A, B and $C=DT^2$ such that the model:

$$\hat{I}_F[kT] = A + B\,\exp\left(-\frac{kT}{\tau}\right) + Ck^2\,\exp\left(-\frac{kT}{\tau}\right) \qquad (7)$$

closely fits the data. The quantity $\tau$ is the ring-down time constant, A is the offset, B is the amplitude of the ring-down waveform and C is the correction, which is necessary to take into account the mode coupling due to backscattering.

In order to reduce the processing time, we first obtain an approximate ring-down time constant $\tau$ by fitting an exponential model without the backscatter correction term:

$$\hat{I}_F[kT] = A' + B'\,\exp\left(-\frac{kT}{\tau'}\right) \qquad (8)$$

and then use the approximate parameter values A', B' and $\tau'$ as the starting point of a single iteration of the Levenberg-Marquardt algorithm for the full model.

Fitting the exponential model can be done using several alternative methods. For efficiency, we prefer an implementation based on a discrete-time modification to the method of successive integration of Matheson (Analytical Instrumentation, 16 (3), 345-373 (1987)), and closely related to the method proposed in "Fast exponential fitting algorithm for real-time instrumental use," by Halmer, Basum, Hering and Muertz, Review of Scientific Instruments, 75, (6), 2187-2191 (2004). This involves calculating first the sum sequence:

$$S[nT] = \sum_{k=0}^{n} I_F[kT] \qquad (9)$$

and then using standard least-squares linear regression to find P, Q and R such that:

$$I_F[nT]=P+QS[nT]+Rn. \qquad (10)$$

We have verified that if $I_F$ has the form given by equation (8), the sum sequence is given by:

$$S[nT] = A'(n+1) + B' \frac{1 - \exp\left(-\frac{(n+1)T}{\tau'}\right)}{1 - \exp\left(-\frac{T}{\tau'}\right)} \qquad (11)$$

$$= \frac{A' + B'}{1 - \exp\left(-\frac{T}{\tau'}\right)} - \frac{I_F[nT]}{\exp\left(\frac{T}{\tau'}\right) - 1} + A'n.$$

Rearranging this into the form of equation (10), we find that:

$$I_F[nT] = (A' + B')\exp\left(\frac{T}{\tau'}\right) - \left[\exp\left(\frac{T}{\tau'}\right) - 1\right]S[nT] + A'\left[\exp\left(\frac{T}{\tau'}\right) - 1\right]n. \qquad (12)$$

Equating coefficients gives us the desired parameter values:

$$\tau' = \frac{T}{\log(1-Q)}, \quad A' = -\frac{R}{Q} \text{ and } B' = \frac{P}{1-Q} + \frac{R}{Q}. \qquad (13)$$

Alternatively, having obtained the values of A', B' and τ', we carry out a single iteration of the nonlinear least-squares Levenberg-Marquardt algorithm for (7). Using the sum-of-squares misfit function, $$E \equiv \sum_{k=0}^{N-1} \left(I_F[kT] - \hat{I}_F[kT;\theta]\right)^2 \qquad (14)$$

where θ=(A, B, C, τ) denotes the vector of parameters to be fitted, this algorithm calculates an improved estimate via $$\theta_{new} = \theta_{old} - \delta\theta \qquad (15)$$

where the components of δθ satisfy the system of equations $$\sum_j \frac{\partial^2 E}{\partial \theta_i \partial \theta_j} \delta\theta_j = \frac{\partial E}{\partial \theta_i}, \qquad (16)$$

the partial derivatives being calculated at $\theta_{old}$. The gradient term is $$\frac{\partial E}{\partial \theta_i} = -2 \sum_{k=0}^{N-1} \left(I_F[kT] - \hat{I}_F[kT]\right) \frac{\partial \hat{I}_F[kT;\theta]}{\partial \theta_i} \qquad (17)$$

while the Hessian term is approximated by the positive-definite matrix $$\frac{\partial^2 E}{\partial \theta_i \partial \theta_j} \approx 2 \sum_{k=0}^{N-1} \frac{\partial \hat{I}_F[kT;\theta]}{\partial \theta_i} \frac{\partial \hat{I}_F[kT;\theta]}{\partial \theta_j}. \qquad (18)$$

These require the computation of the elements of the Jacobian of the model, $$\frac{\partial \hat{I}_F}{\partial A} = 1 \qquad (19)$$

$$\frac{\partial \hat{I}_F}{\partial B} = \exp\left(-\frac{kT}{\tau}\right)$$

$$\frac{\partial \hat{I}_F}{\partial B} = k^2 \exp\left(-\frac{kT}{\tau}\right)$$

$$\frac{\partial \hat{I}_F}{\partial \tau} = \frac{(B + Ck^2)kT}{\tau^2} \exp\left(-\frac{kT}{\tau}\right)$$

at the location of the intial parameter estimate, namely A=A', B=B', C=0 and τ=τ'.

Computation of δθ involves the inversion of the 4×4 Hessian matrix. The elements of this matrix may be calculated analytically, and the inverse matrix pre-computed and stored, which further speeds up the algorithm.

Although the modified fitting algorithm I have developed allows the cavity absorption to be better estimated even in the presence of the backwards-propagating wave, I have found that it is still advantageous to reduce as much as possible, the amplitude of this extraneous wave. In the absence of a backwards-propagating wave, the ringdown waveform is a pure exponential decay, which has the property that its shape is unchanged when the time-origin is shifted. When the backwards-propagating wave is present, the independence of the time-origin in no longer holds, and the estimate of the absorption depends also on the time at which the backwards wave begins to build up. When the amplitude of the backwards wave is large, the variability of the position of the time origin causes a large uncertainty in the estimated absorption, reducing the sensitivity of the measurement.

A second aspect of this invention involves an apparatus for measuring the intensity of the backwards-propagating wave in a ring-down cavity. From equation (2), the intensity of this wave is given by:

$$I_B = |E_B|^2 = \exp(-2\gamma_r t)|\sin h \, \kappa t|^2 = \exp(-2\gamma_r t)[\sin h^2 \kappa_r t + \sin^2 \kappa_i t], \qquad (20)$$

In the limit of small absolute value of κ, this may be approximated by $I_B \approx |\kappa|^2 t^2 \exp(-2\gamma_r t)$, which has a peak value of $|\kappa|^2/(\gamma_r e)^2$. The peak intensity of the backwards-propagating wave thus provides a direct measure of the coupling between

Figure 6:
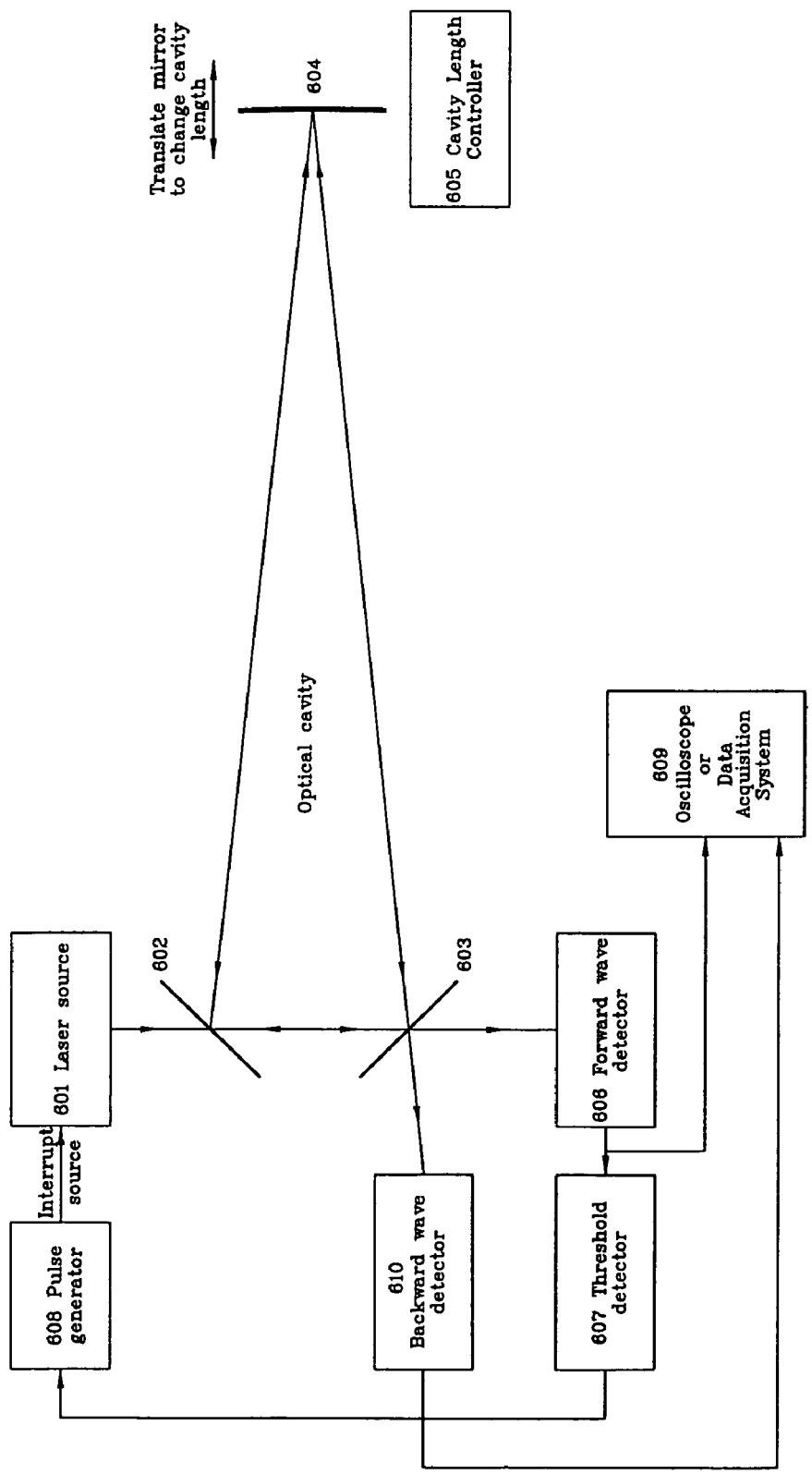
FIG. 6 shows a CRDS system, modified in accordance with the present invention to monitor both forwards and backwards waves during cavity ring-downs.

|κ| the counter-propagating modes. In FIG. 6, a modified CRDS system configured for monitoring the backwards wave in a cavity is shown. Since the backwards wave is caused by scattering of the laser light by imperfections in the cavity mirrors, such a backwards-wave monitor may be utilized during the cavity construction process to optimize the placement of the mirrors. By adjusting the mirror positions so as to minimize the amplitude of the backwards-propagating wave as measured by the detector while the cavity is ringing down, scattering of the beam off the mirror imperfections can be reduced to the maximum extent possible. The effect of this procedure is to produce cavities with both improved shot-to-shot repeatability of ringdown times and improved sensitivity.

A portion of the configuration shown in FIG. 6 consists of a three-mirror CRDS system for collecting cavity ring-down data. The laser source 601 produces light that is directed towards the input mirror of an optical cavity consisting of mirrors 602, 603 and 604. The shape and polarization of the light beam are adjusted using known techniques so that the incident field matches a mode consisting of a wave that propagates anticlockwise around the cavity. The length of the cavity may be adjusted by translating mirror 604 such as by a piezo-electric transducer, under the control of unit 605. This controller brings the frequency of the cavity mode into resonance with the light, causing a build up of the light circulating within the cavity. Forward wave photodetector 606 monitors a portion of the light in the anticlockwise propagating mode that is transmitted through output mirror 603. When the intensity of the light exceeds a preset threshold, unit 607 produces an output signal that instructs pulse generator 608 to turn off the laser source for a period of time during which the ringdown waveform measured by forward-wave detector 606 is recorded and processed by unit 609. After the cavity has rung down completely, unit 608 turns the laser 601 back on again, in preparation for the next ring-down event.

The modification to the system in accordance with the present invention consists of the addition of backwards wave photodetector 610 that collects a portion of the light that is propagating clockwise within the cavity, and which leaves the cavity through mirror 603. As described earlier, the clockwise propagating light arises due to scattering of the light off imperfections in the mirrors. The output of detector 610 is recorded (by unit 609) in time synchronization with the ringdown waveform collected by detector 606. By examining the peak of the backwards wave intensity during the ring-down period, the coupling between the forwards and backwards propagating modes may be minimized by adjusting the cavity mirrors. Moreover, if the scattering imperfections on the mirrors at a given wavelength cannot be completely eliminated through the mirror production process, then the backscatter monitor can be used in an operating CRDS system to mitigate for the increased uncertainty in the ring-down waveform. This monitor can also be used to watch the cavity degradation over time, and serve as an early indicator for cavity failure. Suitable photodetectors include photodiodes, photomultipliers and avalanche photodiodes.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general. Figures are schematic only and are not intended to constitute an accurate geometric portrayal of the location of the elements shown. Further, while the present invention has been particularly described in terms of certain preferred embodiments, the invention is not limited to such preferred embodiments. Rather, the scope of the invention is defined by the appended claims.

The invention claimed is:

1. A method for determining the ringdown time constant $\tau$ of the measurement performed by a cavity ringdown spectrometer by fitting the discrete function $I_F[kT]$ in accordance with the equation:

$$I_F[kT]=A+B\exp(-kT/\tau)+Ck^2\exp(-kT/\tau)$$

wherein T is the sampling time, k is the sequence index, A represents the offset in the ringdown detector electronics, B represents the amplitude of the ringdown waveform and C is the correction which takes account of the mode coupling due to backscattering.

2. A method in accordance with claim 1 for determining the ringdown time constant $\tau$ of the measurement performed by a cavity ringdown spectrometer by first fitting the discrete function: $I_F[kT]=A'+B'\exp(-kT/\tau')$ which does not include the backscattering term and utilizing the values of A', B' and $\tau'$ as initial values for a single iteration fit in the equation:

$$I_F[kT]=A+B\exp(-kT/\tau)+Ck^2\exp(-kT/\tau).$$

3. A method in accordance with claim 2 wherein said first fitting is performed using the successive integration method of Matheson.

4. A method in accordance with claim 2 wherein said first fitting is performed using the modified successive integration method of Halmer.

5. A method in accordance with claim 2 wherein said single iteration fit is performed using the non-linear least squares fitting method of Levenberg-Marquardt.

* * * * *